United States Patent [19]
Ruegg et al.

[11] Patent Number: 5,998,599
[45] Date of Patent: Dec. 7, 1999

[54] GROWTH ARREST GENE COMPOSITIONS AND METHODS

[75] Inventors: Curtis L. Ruegg, Redwood City; Reiner Laus, San Carlos; Edgar G. Engleman, Atherton, all of Calif.

[73] Assignee: Dendreon Corporation, Seattle, Wash.

[21] Appl. No.: 08/883,070

[22] Filed: Jun. 27, 1997

Related U.S. Application Data

[60] Provisional application No. 60/021,874, Jun. 28, 1996.
[51] Int. Cl.$^6$ ............... C12N 1/21; C12N 5/10; C12N 15/12; C12N 15/63
[52] U.S. Cl. ............... 536/23.5; 435/320.1; 435/325; 435/252.3; 435/455; 435/471
[58] Field of Search .................. 536/23.1, 23.5; 435/320.1, 325, 252.3, 455, 471

[56] References Cited

U.S. PATENT DOCUMENTS 5,399,346  3/1995  Anderson et al. ............... 424/93.21

FOREIGN PATENT DOCUMENTS

WO 97/19171  5/1997  WIPO .

OTHER PUBLICATIONS

Ben–Porath, Ittai and Nissim Benvenisty, "Characterization of a tumor–associated gene, a member of a novel family of genes encoding membrane glycoproteins," Gene 183:69–75 (1996).

Koenig, Scott, "A lesson from the HIV patient: The immune response is still the bane (or promise) of gene therapy," Nature Medicine 2(2): 165–167 (1996).

Marvin, K.W., et al., "Identification and Characterization of a Novel Squamous Cell–associated Gene Related to PMP22," The Journal of Biological Chemistry 270(48):28910–28916 (1995).

Patel, Pragna I., et al., "The gene for the peripheral myelin protein PMP–22 is a candidate for Charcot–Marie–Tooth disease type 1A," Nature Genetics 1:159–165 (1992).

Riddell, S.R., et al., "T–cell medicated rejection of gene–modified HIV–specific cytotoxic T lymphocytes in HIV infected patients," Nature Medicine 2(2):216–223 (1996).

Ruegg, C.L., et al., "B4B, a Novel Growth–Arrest Gene, Is Expressed by a Subset of Progenitor/Pre–B Lymphocytes Negative for Cytoplasmic $\mu$–Chain," The Journal of Immunology 157:72–80 (1996).

Taylor, Verdon, et al., "Epithelial Membrane Protein–1, Peripheral Myelin Protein 22, and Lens Membrane Protein 20 Define a Novel Gene Family," The Journal of Biological Chemistry, 270(48):28824–28833 (1995).

*Primary Examiner*—Elizabeth Kemmerer
*Attorney, Agent, or Firm*—Carol A. Stratford; Linda R. Judge; Dehlinger & Associates

[57] ABSTRACT

Disclosed is a novel gene and growth arrest gene product encoded by the gene. Expression of the growth arrest gene B4B results in inhibition of cellular proliferation. The gene and gene product serve as markers of cancerous or pre-cancerous conditions, and as markers of immune states.

8 Claims, 5 Drawing Sheets

```
CCGCATACTT CCAGAAGAGC GGACCAGGGC TGCTGCCAGC ACCTGCCACT     50
CAGAGCGCCT CTGTCGCTGG GACCCTTCAG AACTCTCTTT GCTCACAAGT    100
TACCAAAAAA AAAAGAGCCA ACATGTTGGT ATTGCTGGCT GGTATCTTTG    150
                               M  L  V  L  L  A  G  I  F  V
TGGTCCACAT CGCTACTGTT ATTATGCTAT TTGTTAGCAC CATTGCCAAT    200
 V  H  I  A  T  V  I  M  L  F  V  S  T  I  A  N
GTCTGGTTGG TTTCCAATAC GGTAGATGCA TCAGTAGGTC TTTGGAAAAA    250
 V  W  L  V  S  N  T  V  D  A  S  V  G  L  W  K  N
CTGTACCAAC ATTAGCTGCA GTGACAGCCT GTCATATGCC AGTGAAGATG    300
 C  T  N  I  S  C  S  D  S  L  S  Y  A  S  E  D  A
CCCTCAAGAC AGTGCAGGCC TTCATGATTC TCTCTATCAT CTTCTGTGTC    350
 L  K  T  V  Q  A  F  M  I  L  S  I  I  F  C  V
ATTGCCCTCC TGGTCTTCGT GTTCCAGCTC TTCACCATGG AGAAGGGAAA    400
 I  A  L  L  V  F  V  F  Q  L  F  T  M  E  K  G  N
CCGGTTCTTC CTCTCAGGGG CCACCACACT GGTGTGCTGG CTGTGCATTC    450
 R  F  F  L  S  G  A  T  T  L  V  C  W  L  C  I  L
TTGTGGGGGT GTCCATCTAC ACTAGTCATT ATGCGAATCG TGATGAACG     500
 V  G  V  S  I  Y  T  S  H  Y  A  N  R  D  G  T
CAGTATCACC ACGGCTATTC CTACATCCTG GCTGGATCT GCTTCTGCTT     550
 Q  Y  H  H  G  Y  S  Y  I  L  G  W  I  C  F  C  F
CAGCTTCATC ATCGGCGTTC TCTATCTGGT CCTGAGAAAG AAATAAGGCC    600
 S  F  I  I  G  V  L  Y  L  V  L  R  K  K  *
GGACGAGTTC ATGGGGATCT GGGGGGTGGG GAGGAGGAAG CCGTTGAATC    650
TGGGAGGGAA GTGGAGGTTG CTGTACAGGA AAAACCGAGA TAGGGGAGGG    700
GGGAGGGGGA AGCAAAGGGG GGAGGTCAAA TCCCAAACCA TTACTGAGGG    750
GATTCTCTAC TGCCAAGCCC CTGCCCTGGG GAGAAGTAG TTGGCTAGTA     800
CTTTGATGCT CCCTTGATGG GGTCCAGAGA GCCTCCCTGC AGCCACCAGA    850
CTTGGCCTCC AGCTGTTCTT AGTGACACAC ACTGTCTGGG GCCCCATCAG    900
CTGCCACAAC ACCAGCCCCA CTTCTGGGTC ATGCACTGAG GTCCACAGAC    950
CTACTGCACT GAGTTAAAAT AGCGGTACAA GTTCTGGCAA GAGCAGATAC   1000
TGTCTTTGTG CTGAATACGC TAAGCCTGGA AGCCATCCTG CCCTTCTGAC   1050
CCAAAGCAAA ACATCACATT CCAGTCTGAA GTGCCACTG GGGGCTTTG     1100
GCCTGTGAGC CATTGTCCCT CTTTGGAACA GATATTTAGC TCTGTGGAAT   1150
TCAGTGACAA AATGGGAGGA GGAAAGAGAG TTTGTAAGGT CATGCTGGTG   1200
GGTTAGCTAA ACCAAGAAGG AGACCTTTTC ACAATGGAAA ACCTGGGGGA   1250
TGGTCAGAGC CCAGTCGAGA CCTCACACAC GGCTGTCCCT CATGGAGACC   1300
TCATGCCATG GTCTTTGCTA GGCCTCTTGC TGAAAGCCAA GGCAGCTCTT   1350
CTGGAGTTTC TCTAAAGTCA CTAGTGAACA ATTCGGTGGT AAAAGTACCA   1400
CACAAACTAT GGGATCCAAG GGGCAGTCTT GCAACAGTGC CATGTTAGGG   1450
TTATGTTTTT AGGATTCCCC TCAATGCAGT CAGTGTTTCT TTTAAGTATA   1500
CAACAGGAGA GAGATGGACA TGGCTCATTG TAGCACAATC CTATTACTCT   1550
TCCTCTAACA TTTTTGAGGA AGTTTTGTCT AATTATCAAT ATTGAGGATC   1600
AGGGCTCCTA GGCTCAGTGG TAGCTCTGGC TTAGACACCA CCTGGAGTGA   1650
TCACCTCTTG GGGACCCTGC CTATCCCACT TCACAGGTGA GGCATGGCAA   1700
TTCTGGAAGC TGATTAAAAC ACACATAAAC CAAAACCAAA CAACAGGCCC   1750
TTGGGTGAAA GGTGCTATAT AATTGTGAAG TATTAAGCCT ACCGTATTTC   1800
AGCCATGATA AGAACAGAGT GCCTGCATTC CCAGGAAAAT ACGAAAATCC   1850
CATGAGATAA ATAAAAATAT AGGTGATGGG CAGATCTTTT CTTTAAAATA   1900
AAAAAGCAAA AACTCTTGTG GTACCTAGTC AGATGGTAGA CGAGCTGTCT   1950
GCTGCCGCAG GAGCACCTCT ATACAGGACT TAGAAGTAGT ATGTTATTCC   2000
TGGTTAAGCA GGCATTGCTT TGCCCTGGAG CAGCTATTTT AAGCCATCTC   2050
AGATTCTGTC TAAAGGGGTT TTTTGGGAAG ACGTTTTCTT TATCGCCCTG   2100
AGAAGATCTA CCCCAGGGAG AATCTGAGAC ATCTTGCCTA CTTTTCTTTA   2150
TTAGCTTTCT CCTCATTCAT TTCTTTTATA CCTTTCCTTT TTGGGGAGTT   2200
GTTATGCCAT GATTTTTGGT ATTTATGTAA AAGGATTATT ACTAATTCTA   2250
TTTCTCTATG TTTATTCTAG TTAAGGAAAT GTTGAGGCA AGCCACCAAA    2300
TTACCTAGGC TGAGGTTAGA GAGATTGGCC AGCAAAAACT GTGGGAAGAT   2350
GAACTTTGTC ATTATGATTT CATTATCACA TGATTATAGA AGGCTGTCTT   2400
AGTGCAAAAA ACATACTTAC ATTTCAGACA TATCCAAAGG GAATACTCAC   2450
ATTTTGTTAA GAAGTTGAAC TATGACTGGA GTAAACCATG TATCCCCTTA   2500
TCTTTTACTT TTTTTCTGTG ACATTTATGT CTCATGTAAT TTGCATTACT   2550
CTGGTGGATT GTTCTAGTAC TGTATTGGGC TTCTTCGTTA ATAGATTATT   2600
TCATATACTA TAATTGTAAA TATTTTGATA CAAATGTTTA TAACTCTAGG   2650
GATATAAAAA CAGATTCTGA TTCCCAAAAA AAAAAAAAAA AAAAAAAAA    2700
AAAAA                                                    2705
```

Fig. 1

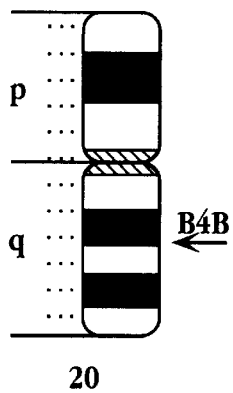

Fig. 2

```
ATCCACAGCC AGCACACCAG CCCAGGAAAC TTATAACCTC GGGAGTCAGG      50
TCCCTCCCCT CACTGTGGTT GCAGATCTCC TGAAGAGAGG ACCAGACCAG     100
CAGCCTGCTC TACCACCCAG GGCATCTGCC TCTCTCACTG GATACTCCAG     150
AATTCTCTAC TCAGAAGTCA CCAAAAAGCC AAGATGTTGG TGCTACTGGC     200
TGGTCTCTTT GTGGTCCACA TTGCCACTGC CATTATGCTG TTTGTCTCCA     250
CCATTGCCAA CGTCTGGATG GTTGCAGATT ACGCAAATGC ATCTGTAGGG     300
CTTTGGAAGA ACTGCACTGG TGGTAACTGC GACGGCTCCC TGTCCTACGG     350
CAATGAAGAT GCTATCAAGG CAGTGCAAGC CTTCATGATC CTCTCCATCA     400
TCTTCTCCAT CATCTCCCTC GTGGTCTTCG TGTTCCAGCT CTTCACTATG     450
GAGAAGGGAA ACCGGTTCTT CCTCTCGGGG TCCACCATGC TGGTGTGCTG     500
GCTGTGTATC CTGGTTGGAG TGTCAATCTA CACTCATCAT TACGCCCACA     550
GCGAAGGGAA CTTCAACTCC AGCAGCCACC AAGGCTATTG TTTCATCCTG     600
ACCTGGATCT GCTTCTGTTT CAGCTTCATC ATCGGCATAC TCTATCTGGT     650
CCTGAGAAAG AAATAA                                         666
```

Fig. 3

```
MLVLLAGLFV VHIATAIMLF VSTIANVWMV ADYANASVGL WKNCTGGNCD      50
GSLSYGNEDA IKAVQAFMIL SIIFSIISLV VFVFQLFTME KGNRFFLSGS    100
TMLVCWLCIL VGVSIYTHHY AHSEGNFNSS SHQGYCFILT WICFCFSFII    150
GILYLVLRKK                                                160
```

Fig. 4

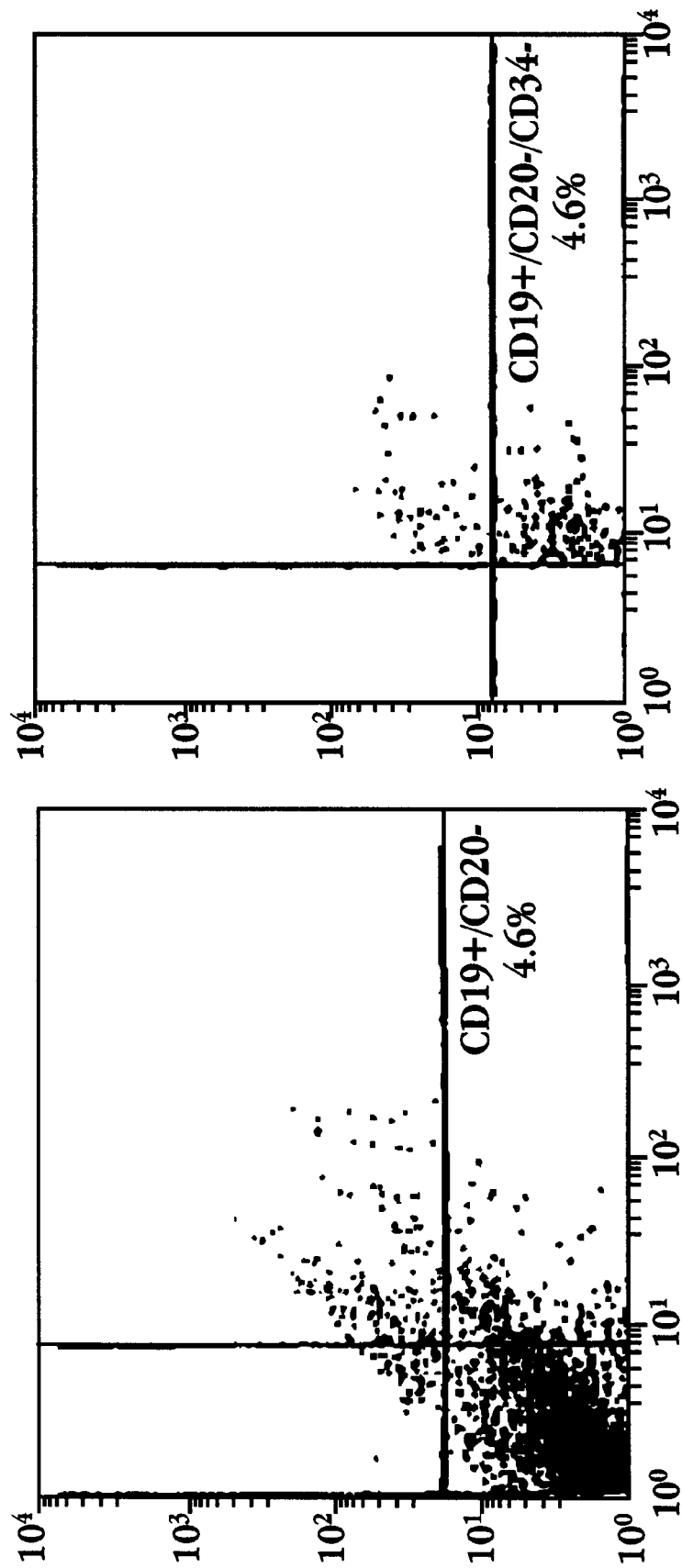

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 2675 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (C) INDIVIDUAL ISOLATE: B4B (xi) SEQUENCE DESCRIPTION: SEQ ID NO:1:

```
CCGCATACTT CCAGAAGAGC GGACCAGGGC TGCTGCCAGC ACCTGCCACT CAGAGCGCCT      60

CTGTCGCTGG GACCCTTCAG AACTCTCTTT GCTCACAAGT TACCAAAAAA AAAAGAGCCA     120

ACATGTTGGT ATTGCTGGCT GGTATCTTTG TGGTCCACAT CGCTACTGTT ATTATGCTAT     180

TTGTTAGCAC CATTGCCAAT GTCTGGTTGG TTTCCAATAC GGTAGATGCA TCAGTAGGTC     240

TTTGGAAAAA CTGTACCAAC ATTAGCTGCA GTGACAGCCT GTCATATGCC AGTGAAGATG     300

CCCTCAAGAC AGTGCAGGCC TTCATGATTC TCTCTATCAT CTTCTGTGTC ATTGCCCTCC     360

TGGTCTTCGT GTTCCAGCTC TTCACCATGG AGAAGGGAAA CCGGTTCTTC CTCTCAGGGG     420

CCACCACACT GGTGTGCTGG CTGTGCATTT TGTGGGGGT GTCCATCTAC ACTAGTCATT     480

ATGCGAATCG TGATGGAACG CAGTATCACC ACGGCTATTC CTACATCCTG GGCTGGATCT     540

GCTTCTGCTT CAGCTTCATC ATCGGCGTTC TCTATCTGGT CCTGAGAAAG AAATAAGGCC     600

GGACGAGTTC ATGGGGATCT GGGGGGTGGG GAGGAGGAAG CCGTTGAATC TGGGAGGGAA     660

GTGGAGGTTG CTGTACAGGA AAAACCGAGA TAGGGGAGGG GGGAGGGGGA AGCAAAGGGG     720

GGAGGTCAAA TCCCAAACCA TTACTGAGGG GATTCTCTAC TGCCAAGCCC CTGCCCTGGG     780

GAGAAAGTAG TTGGCTAGTA CTTTGATGCT CCCTTGATGG GGTCCAGAGA GCCTCCCTGC     840
```

| | |
|---|---|
| AGCCACCAGA CTTGGCCTCC AGCTGTTCTT AGTGACACAC ACTGTCTGGG GCCCCATCAG | 900 |
| CTGCCACAAC ACCAGCCCCA CTTCTGGGTC ATGCACTGAG GTCCACAGAC CTACTGCACT | 960 |
| GAGTTAAAAT AGCGGTACAA GTTCTGGCAA GAGCAGATAC TGTCTTTGTG CTGAATACGC | 1020 |
| TAAGCCTGGA AGCCATCCTG CCCTTCTGAC CCAAAGCAAA ACATCACATT CCAGTCTGAA | 1080 |
| GTGCCTACTG GGGGCTTTG GCCTGTGAGC CATTGTCCCT CTTTGGAACA GATATTTAGC | 1140 |
| TCTGTGGAAT TCAGTGACAA AATGGGAGGA GGAAAGAGAG TTTGTAAGGT CATGCTGGTG | 1200 |
| GGTTAGCTAA ACCAAGAAGG AGACCTTTTC ACAATGGAAA ACCTGGGGGA TGGTCAGAGC | 1260 |
| CCAGTCGAGA CCTCACACAC GGCTGTCCCT CATGGAGACC TCATGCCATG GTCTTTGCTA | 1320 |
| GGCCTCTTGC TGAAAGCCAA GGCAGCTCTT CTGGAGTTTC TCTAAAGTCA CTAGTGAACA | 1380 |
| ATTCGGTGGT AAAAGTACCA CACAAACTAT GGGATCCAAG GGGCAGTCTT GCAACAGTGC | 1440 |
| CATGTTAGGG TTATGTTTTT AGGATTCCCC TCAATGCAGT CAGTGTTTCT TTTAAGTATA | 1500 |
| CAACAGGAGA GAGATGGACA TGGCTCATTG TAGCACAATC CTATTACTCT TCCTCTAACA | 1560 |
| TTTTTGAGGA AGTTTTGTCT AATTATCAAT ATTGAGGATC AGGGCTCCTA GGCTCAGTGG | 1620 |
| TAGCTCTGGC TTAGACACCA CCTGGAGTGA TCACCTCTTG GGACCCTGC CTATCCCACT | 1680 |
| TCACAGGTGA GGCATGGCAA TTCTGGAAGC TGATTAAAAC ACACATAAAC CAAAACCAAA | 1740 |
| CAACAGGCCC TTGGGTGAAA GGTGCTATAT AATTGTGAAG TATTAAGCCT ACCGTATTTC | 1800 |
| AGCCATGATA AGAACAGAGT GCCTGCATTC CCAGGAAAAT ACGAAAATCC CATGAGATAA | 1860 |
| ATAAAAATAT AGGTGATGGG CAGATCTTTT CTTTAAAATA AAAAAGCAAA AACTCTTGTG | 1920 |
| GTACCTAGTC AGATGGTAGA CGAGCTGTCT GCTGCCGCAG GAGCACCTCT ATACAGGACT | 1980 |
| TAGAAGTAGT ATGTTATTCC TGGTTAAGCA GGCATTGCTT TGCCCTGGAG CAGCTATTTT | 2040 |
| AAGCCATCTC AGATTCTGTC TAAAGGGGTT TTTTGGGAAG ACGTTTTCTT TATCGCCCTG | 2100 |
| AGAAGATCTA CCCCAGGGAG AATCTGAGAC ATCTTGCCTA CTTTTCTTTA TTAGCTTTCT | 2160 |
| CCTCATTCAT TTCTTTTATA CCTTTCCTTT TTGGGGAGTT GTTATGCCAT GATTTTTGGT | 2220 |
| ATTTATGTAA AAGGATTATT ACTAATTCTA TTTCTCTATG TTTATTCTAG TTAAGGAAAT | 2280 |
| GTTGAGGGCA AGCCACCAAA TTACCTAGGC TGAGGTTAGA GAGATTGGCC AGCAAAAACT | 2340 |
| GTGGGAAGAT GAACTTTGTC ATTATGATTT CATTATCACA TGATTATAGA AGGCTGTCTT | 2400 |
| AGTGCAAAAA ACATACTTAC ATTTCAGACA TATCCAAAGG GAATACTCAC ATTTTGTTAA | 2460 |
| GAAGTTGAAC TATGACTGGA GTAAACCATG TATCCCCTTA TCTTTTACTT TTTTTCTGTG | 2520 |
| ACATTTATGT CTCATGTAAT TTGCATTACT CTGGTGGATT GTTCTAGTAC TGTATTGGGC | 2580 |
| TTCTTCGTTA ATAGATTATT TCATATACTA TAATTGTAAA TATTTTGATA CAAATGTTTA | 2640 |
| TAACTCTAGG GATATAAAAA CAGATTCTGA TTCCC | 2675 |

(2) INFORMATION FOR SEQ ID NO:2:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: B4B (xi) SEQUENCE DESCRIPTION: SEQ ID NO:2:

| | |
|---|---|
| ATGTTGGTAT TGCTGGCTGG TATCTTTGTG GTCCACATCG CTACTGTTAT TATGCTATTT | 60 |

```
GTTAGCACCA TTGCCAATGT CTGGTTGGTT TCCAATACGG TAGATGCATC AGTAGGTCTT      120

TGGAAAAACT GTACCAACAT TAGCTGCAGT GACAGCCTGT CATATGCCAG TGAAGATGCC      180

CTCAAGACAG TGCAGGCCTT CATGATTCTC TCTATCATCT TCTGTGTCAT TGCCCTCCTG      240

GTCTTCGTGT TCCAGCTCTT CACCATGGAG AAGGGAAACC GGTTCTTCCT CTCAGGGGCC      300

ACCACACTGG TGTGCTGGCT GTGCATTCTT GTGGGGGTGT CCATCTACAC TAGTCATTAT      360

GCGAATCGTG ATGGAACGCA GTATCACCAC GGCTATTCCT ACATCCTGGG CTGGATCTGC      420

TTCTGCTTCA GCTTCATCAT CGGCGTTCTC TATCTGGTCC TGAGAAAGAA A               471
```

(2) INFORMATION FOR SEQ ID NO:3:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (vi) ORIGINAL SOURCE:
        (C) INDIVIDUAL ISOLATE: B4B (xi) SEQUENCE DESCRIPTION: SEQ ID NO:3:

```
Met Leu Val Leu Leu Ala Gly Ile Phe Val Val His Ile Ala Thr Val
1               5                   10                  15

Ile Met Leu Phe Val Ser Thr Ile Ala Asn Val Trp Leu Val Ser Asn
            20                  25                  30

Thr Val Asp Ala Ser Val Gly Leu Trp Lys Asn Cys Thr Asn Ile Ser
            35                  40                  45

Cys Ser Asp Ser Leu Ser Tyr Ala Ser Glu Asp Ala Leu Lys Thr Val
50                  55                  60

Gln Ala Phe Met Ile Leu Ser Ile Ile Phe Cys Val Ile Ala Leu Leu
65                  70                  75                  80

Val Phe Val Phe Gln Leu Phe Thr Met Glu Lys Gly Asn Arg Phe Phe
                85                  90                  95

Leu Ser Gly Ala Thr Thr Leu Val Cys Trp Leu Cys Ile Leu Val Gly
                100                 105                 110

Val Ser Ile Tyr Thr Ser His Tyr Ala Asn Arg Asp Gly Thr Gln Tyr
            115                 120                 125

His His Gly Tyr Ser Tyr Ile Leu Gly Trp Ile Cys Phe Cys Phe Ser
        130                 135                 140

Phe Ile Ile Gly Val Leu Tyr Leu Val Leu Arg Lys Lys
145                 150                 155
```

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:4:

```
Cys Ser Asp Ser Leu Ser Tyr Ala Ser Glu Asp Ala Leu Lys
1               5                   10
```

(2) INFORMATION FOR SEQ ID NO:5:

(i) SEQUENCE CHARACTERISTICS:
        (A) LENGTH: 13 amino acids (B) TYPE: amino acid
            (D) TOPOLOGY: linear (ii) MOLECULE TYPE: peptide (xi) SEQUENCE DESCRIPTION: SEQ ID NO:5:

Ser His Tyr Ala Asn Arg Asp Gly Thr Gln Tyr His His
1               5                   10

(2) INFORMATION FOR SEQ ID NO:6:

(i) SEQUENCE CHARACTERISTICS:
            (A) LENGTH: 666 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (C) INDIVIDUAL ISOLATE: murine B4B coding region (xi) SEQUENCE DESCRIPTION: SEQ ID NO:6:

ATCCACAGCC AGCACACCAG CCCAGGAAAC TTATAACCTC GGGAGTCAGG TCCCTCCCCT        60

CACTGTGGTT GCAGATCTCC TGAAGAGAGG ACCAGACCAG CAGCCTGCTC TACCACCCAG       120

GGCATCTGCC TCTCTCACTG GATACTCCAG AATTCTCTAC TCAGAAGTCA CCAAAAAGCC       180

AAGATGTTGG TGCTACTGGC TGGTCTCTTT GTGGTCCACA TTGCCACTGC CATTATGCTG       240

TTTGTCTCCA CCATTGCCAA CGTCTGGATG GTTGCAGATT ACGCAAATGC ATCTGTAGGG       300

CTTTGGAAGA ACTGCACTGG TGGTAACTGC GACGGCTCCC TGTCCTACGG CAATGAAGAT       360

GCTATCAAGG CAGTGCAAGC CTTCATGATC CTCTCCATCA TCTTCTCCAT CATCTCCCTC       420

GTGGTCTTCG TGTTCCAGCT CTTCACTATG GAGAAGGGAA ACCGGTTCTT CCTCTCGGGG       480

TCCACCATGC TGGTGTGCTG GCTGTGTATC CTGGTTGGAG TGTCAATCTA CACTCATCAT       540

TACGCCCACA GCGAAGGGAA CTTCAACTCC AGCAGCCACC AAGGCTATTG TTTCATCCTG       600

ACCTGGATCT GCTTCTGTTT CAGCTTCATC ATCGGCATAC TCTATCTGGT CCTGAGAAAG       660

AAATAA                                                                  666

(2) INFORMATION FOR SEQ ID NO:7:

(i) SEQUENCE CHARACTERISTICS:
            (A) LENGTH: 160 amino acids
            (B) TYPE: amino acid
            (D) TOPOLOGY: linear (ii) MOLECULE TYPE: peptide (vi) ORIGINAL SOURCE:
            (C) INDIVIDUAL ISOLATE: murine B4B (xi) SEQUENCE DESCRIPTION: SEQ ID NO:7:

Met Leu Val Leu Leu Ala Gly Leu Phe Val Val His Ile Ala Thr Ala
1               5                   10                  15

Ile Met Leu Phe Val Ser Thr Ile Ala Asn Val Trp Met Val Ala Asp
                20                  25                  30

Tyr Ala Asn Ala Ser Val Gly Leu Trp Lys Asn Cys Thr Gly Gly Asn
            35                  40                  45

Cys Asp Gly Ser Leu Ser Tyr Gly Asn Glu Asp Ala Ile Lys Ala Val
        50                  55                  60

Gln Ala Phe Met Ile Leu Ser Ile Ile Phe Ser Ile Ile Ser Leu Val
65                  70                  75                  80

```
Val Phe Val Phe Gln Leu Phe Thr Met Glu Lys Gly Asn Arg Phe Phe
            85              90                  95

Leu Ser Gly Ser Thr Met Leu Val Cys Trp Leu Cys Ile Leu Val Gly
            100             105             110

Val Ser Ile Tyr Thr His His Tyr Ala His Ser Glu Gly Asn Phe Asn
            115             120             125

Ser Ser Ser His Gln Gly Tyr Cys Phe Ile Leu Thr Trp Ile Cys Phe
            130             135             140

Cys Phe Ser Phe Ile Ile Gly Ile Leu Tyr Leu Val Leu Arg Lys Lys
145             150             155             160
```

GROWTH ARREST GENE COMPOSITIONS AND METHODS

This application claims the benefit of U.S. Provisional Application No. 60/021,874 filed Jun. 28, 1996, incorporated herein by reference.

FIELD OF THE INVENTION

The invention relates to a novel nucleotide coding sequence that encodes a novel growth arrest factor, to the factor, to cells expressing the gene product, as well as to methods for producing the foregoing compositions.

REFERENCES

Ausubel, F.M., et al., in *CURRENT PROTOCOLS IN MOLECULAR BIOLOGY*, John Wiley & Sons, Inc., Media, Pa. (1988).
Engleman, E. G., et al., *J. Immunol.* 127:2124 (1981).
Liang, P., and Pardee, A., *Science* 257:967 (1992).
Liu, C. P., et al., *J. Immunol.* 144:1544 (1990).
Matsunami, N., et al., *Nature Genetics* 1:176 (1992).
Patel, P. I., et al., *Nature Genetics* 1:159 (1992).
Ruegg, C. L., et al., *J. Immunol.* 154:4434 (1995).
Ruegg, C. L., et al., *J. Biol. Chem.* 267:18837 (1992).
Timmerman, V., et al., *Nature Genetics* 1:171 (1992).
Valentijin, L. J., et al., *Nature Genetics* 1:166 (1992).
White, B. A., ed., *PCR Cloning Protocols, (Methods in Molecular Biology* 67), Humana Press, Totowa, N.J. 1997.
Wright, M. D., & Tomlinson, M. G., *Immunol. Today* 15:588 (1994).
Yang, N. S., et al., *Proc. Natl. Acad. Sci. USA* (Jun. 25, 1996).

BACKGROUND OF THE INVENTION

B lymphocyte development and differentiation are important in establishing and maintaining the immune response in mammalian species. Mature, immunoglobulin-secreting B cells are the end result of a complex process of differentiation from hematopoietic progenitors that originate in the bone marrow.

The differentiation program of B lymphocytes involves a complex set of molecular signals, perhaps the most fundamental of which is productive rearrangement of the immunoglobulin (Ig) variable domain genetic locus. During B cell ontogeny, productive rearrangement of the Ig gene locus appears to be the central event permitting progression of B cell differentiation to the mature stages of the memory B cell and Ig-secreting plasma cell; however, correct joining of the V, D and J regions of the heavy chain variable domain with the C region to form functional heavy chain polypeptides does not occur in every progenitor B cell.

While positive selection is thought to facilitate continued viability and expansion of B cells possessing productive Ig rearrangements, it has been shown that uncharacterized mechanisms of negative selection, other than apoptosis regulated by bcl-2 and fas, are also involved in the elimination of cells containing nonproductive Ig gene rearrangements (Tarlinton, 1994). In fact, a majority of candidate B cells fail in this early differentiative step and are eliminated from the B cell repertoire. In contrast, and possibly as a result of the breakdown of the various forms of elimination, cells in almost any stage of B cell differentiation are known to undergo neoplastic immortalization, resulting in the appearance of various forms of leukemia and lymphoma when the body's ability to identify and destroy such cells breaks down (Lukens, 1993). Thus, means for early detection of malformed cells would be useful in effecting early diagnosis and treatment of leukemia. Forming the basis for the present invention is the identification of a novel gene, termed "B4B." Even though expression of B4B mRNA can be detected in multiple tissues, expression of the protein which is encoded by the B4B gene is tightly restricted to a subset of progenitor/pre-B cells which do not express cytoplasmic $\mu$-chains. Such cells may therefore lack productive Ig gene rearrangements, and may be superfluous to the body. According to an important feature of the present invention it is further recognized that expression in cells of B4B induces inhibition of cellular growth. Accordingly, B4B antigen expression serves as a useful cell marker, and induction of such expression may prevent unwanted cellular proliferation. These and other useful features of the invention are described in the sections that follow.

SUMMARY OF THE INVENTION

In one aspect, the invention includes isolated DNA molecules that encode B4B growth arrest family gene products. More particularly, the invention includes isolated genes that encode growth arresting gene product having amino acid sequences characterized by at least 50%, and preferably 75% or greater, sequence identity with a protein having an amino acid sequence selected from the sequences presented as SEQ ID NO: 3 and SEQ ID NO: 7. In a preferred embodiment, the isolated DNA molecule encompassed by the invention encodes a growth arrest gene product that is capable of inhibition of proliferation of a host cell, when the gene is expressed by said host cell. It is noted that the DNA comprising the expressible gene may include introns, or may simply include the uninterrupted open reading frame of the genes described herein. The invention is also meant to encompass RNA molecules corresponding to such gene sequences and their uses in the various aspects of the invention described below.

In another embodiment, the isolated DNA molecule of the invention hybridizes with a probe which also hybridizes with SEQ ID NO: 2 or SEQ ID NO: 6. Here, all hybridizations are carried out under moderate stringency conditions to detect DNA sequences having at least 50% sequence identity, and preferably at least 75% sequence identity with the reference sequences. In preferred embodiments, the DNA molecule of the invention has the sequence SEQ ID NO: 2 or the sequence SEQ ID NO: 6.

In a related aspect, the invention includes an isolated B-cell protein antigen characterized by (i) inhibition of proliferation of eukaryotic cells, such as COS-7 cells, when the antigen is transfected into and expressed by such cells, and (ii) at least 50% sequence identity, and preferably at least 75% identity, with a protein selected from the group consisting of a proteins having sequences presented as SEQ ID NO: 3 and SEQ ID NO: 6. In another embodiment, the protein is expressed by B-cells that also express CD19, CD45 and HLA-DR but which do not express CD20, CD3, CD16 or CD56. The antigen preferably has the amino acid sequence SEQ ID NO: 3 or SEQ ID NO: 7.

In still another related aspect, the invention includes an expression vector containing a DNA molecule that encodes a B4B gene product having a sequence that is characterized by at least 50% sequence identity, and preferably at least 75% identity, with a protein having an amino acid sequence selected from the group consisting of SEQ ID NO: 3 and SEQ ID NO: 7. Preferred forms of the vector include polynucleotide coding regions as described for the DNA molecule discussed above.

In a related embodiment, the invention includes a eukaryotic cell, which cell includes a heterologous DNA molecule comprising a sequence of nucleotides that encodes a B4B gene product having at least 50% identity, and preferably at least 75% identity, to a protein having an amino acid sequence selected from the sequences presented as SEQ ID NO: 3 and SEQ ID NO: 7.

In a preferred embodiment, the cell contains a DNA molecule having a sequence selected from the sequences presented as SEQ ID NO: 2 and SEQ ID NO: 6.

The invention also encompasses prokaryotic cells capable of expressing the B4B protein antigens discussed above.

In still another related aspect, the invention includes a method of producing a cell that produces a growth arrest gene product that is capable of inhibition of proliferation of a host cell, i.e., by expressing a B4B growth arrest gene product as described herein. The cell is made by transfecting it with an expression vector that contains a coding region comprising a sequence of nucleotides that encodes a B4B gene product having a sequence that is characterized by at least 50% sequence identity, and preferably at least 75% identity, with a protein having a sequence selected from SEQ ID NO: 3 and SEQ ID NO: 7. In a preferred embodiment, the coding region incorporated into the cell includes the sequence presented as SEQ ID NO: 2 or SEQ ID NO: 6.

In still another related aspect, the invention includes a method of detecting the presence of a subset of cells containing a B4B antigen in a mixture of cells. the method includes contacting the cell mixture with an antibody which is immunoreactive with a protein having the sequence SEQ ID NO: 3, and detecting binding of the antibody to cells in the cell mixture. In a preferred embodiment, the antibody is an antibody directed to a peptide selected from the group consisting of a peptide having the amino acid sequence SEQ ID NO: 4 and a peptide having the amino acid sequence SEQ ID NO: 5. Other methods of detection utilizing the discoveries of the present invention, including detection by amplification assays such as polymerase chain reaction (PCR), also form part of the invention.

The invention further includes the B4B+ cell type and antibodies directed against the B4B gene product and or fragments thereof, as well as diagnostic kits that utilize the nucleotide sequences, antigens and/or antibodies described herein.

These and other objects and features of the invention will become more fully apparent when the following detailed description of the invention is read in conjunction with the accompanying drawings.

BRIEF DESCRIPTION OF THE FIGURES

FIG. 1. shows nucleotide sequence (SEQ ID NO: 1) and deduced amino acid sequence (SEQ ID NO: 3) of the B4B cDNA clone, where the open reading frame constitutes nt 123 to nt 593 (SEQ ID NO: 2) predicted transmembrane regions of the protein are underlined, the amino acid residues comprising Peptide 1 (CSDSLSYASEDALK; SEQ ID NO: 4) and Peptide 2 (SHYANRDGTQYHH; SEQ ID NO: 5) are italicized, potential N-glycosylation sites are shown in boldface type, and the DNA sequence contained within the 101-bp DD-PCR fragment is underlined;

FIG. 2 shows a schematic representation of the chromosomal localization of the B4B gene as determined by fluorescence in situ hybridization using a human B4B genomic probe or a combination of the B4B probe and a probe specific for the centromeric region of human chromosome 20;

FIG. 3 shows the nucleotide sequence of a murine B4B coding region (SEQ ID NO: 6);

FIG. 4 shows the amino acid sequence encoded by SEQ ID NO: 6 as SEQ ID NO: 7;

FIG. 5(A–B) shows flow cytometric analysis plots of normal human bone marrow mononuclear cells stained with CD34-FITC, CD20-PE and CD19-Tricolor and subjected to multi-parameter analysis, where quadrant gates were set to exclude 99.9% of cells stained with irrelevant isotype-matched control mAb, and in (A) cells were analyzed for expression of CD19 (x-axis) and CD20 (y-axis), while panel (B) shows a re-plot of cells in the lower right quadrant (CD19+CD20–) of (A) for expression of CD19 (x-axis) and CD34 (y-axis), and percentage values (4.6%, 3.7%) refer to the fraction of total cells bearing the corresponding phenotype;

DETAILED DESCRIPTIONS OF THE INVENTION

I. Definitions

Figure 6A:
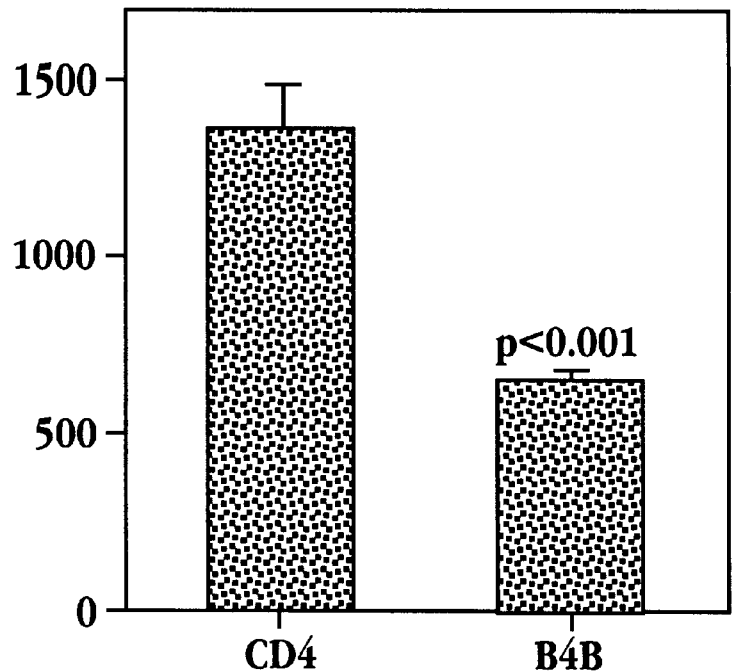
FIG. 6A shows the effect of B4B or CD34 expression on cellular proliferation in transfected COS-7 cells in a thymidine incorporation assay.

Unless otherwise indicated, all terms used herein have the same meaning as they would to one skilled in the art of the present invention. Practitioners are particularly directed to *Current Protocols in Molecular Biology* (Ausubel, et al., 1988) for definitions and terms of the art.

The terms "heterologous DNA" and "heterologous RNA" refer to nucleotides that are not endogenous to the cell in which they are present; generally such nucleotides have been added to the cell by transfection, microinjection, electroporation, or the like. Such nucleotides generally include at least one coding sequence.

The term "vector" or "expression vector" refers to vectors that have the ability to incorporate and express heterologous DNA fragments in a foreign cell. Many prokaryotic and eukaryotic expression vectors are commercially available. Selection of appropriate expression vectors and promoters is within the knowledge of those having skill in the art.

By "B4B growth arrest gene family" is meant a set of genes that encode proteins characterized by: (i) four distinct regions of consisting predominantly of hydrophobic amino acids, (ii) at least 50%, and preferably 75% or greater, sequence identity with the B4B gene product shown as SEQ ID NO: 3 or SEQ ID NO: 7 herein, and (iii) ability to inhibit growth (replication) of a cell, when the gene product is expressed by a cell, or when it is inserted into a cell. Examples of such protein gene products include human and murine forms of B4B, as described herein.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "gene" generally refers to the entire nucleic acid sequence that is necessary for the synthesis of a functional polypeptide or RNA molecule. A gene may include untranslated regions, such as introns. References herein to claimed gene sequences or coding regions are intended to cover the coding region including any untranslated regions (introns) that may be inserted within the coding region.

The term "polypeptide" as used herein refers to a compound made up of a single chain of amino acid residues linked by peptide bonds. The term "protein" may be synonymous with the term "polypeptide" or may refer, in addition to a complex of two or more polypeptides.

As used herein, the terms "substantial homology" or "substantial identity", and declinations thereof, refer to concordance of an amino acid sequence with another amino acid sequence or of a polynucleotide sequence with another polynucleotide sequence of at least 50% and preferably, at least about 75–80% or greater, when such sequences are arranged in a best fit alignment. In the case of nucleotide sequences, the terms imply that the nucleotide sequence in question is capable of being detected in a screening assay by a hybridization probe derived from the nucleotide sequences defined as SEQ ID NO: 1, SEQ ID NO: 2 or SEQ ID NO: 6, under moderately high stringency conditions.

By "moderately high" stringency conditions is generally meant hybridization of probes to target DNA in the presence of between about 50% formamide and about 25–30% formamide at constant temperature (generally, about 42° C.). More specifically, such hybridization will be carried out in the presence of incremental increases in formamide concentration over the stated range.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; X, hydroxyproline; Y, tyrosine.

II. B4B Gene and Gene Product

A. Isolation of B4B Gene and Related Nucleotide Sequences

For use in the present invention, the B4B gene can be isolated by any of a number of methods known in the art from clonal libraries or natural sources. As exemplified below, the gene can be isolated from peripheral blood mononuclear cell (PBMC) fractions. Alternatively, with the guidance of the present specification, polynucleotides can be synthesized by conventional methods, such as using a Applied BioSystems DNA synthesizer (Model 394).

In addition, related nucleotide sequences can be designed to provide for expression of B4B growth arrest family proteins using S known amino acid substitution principles and/or codon usage tables, according to methods well known in the art. Such sequences may be produced synthetically.

1. Isolation of B4B Gene from Peripheral Blood Mononuclear Cell Fractions

Examples 1 and 2 describe how a gene that encodes a B4B gene product is identified in and isolated from peripheral blood mononuclear cells (PBMC). In the examples, the PBMC used were human; however they may be derived from any of a number of sources, and particularly from other mammalian species. Briefly, PBMC are isolated according to standard methods and are fractionated using a density gradient method. The PBMC are centrifuged on a PERCOLL (Pharmacia, Piscataway, N.J.) density step gradient consisting of 30%, 40%, 50.5% and 75% PERCOLL. Cells that fractionate to the interface between the 40% and 50.5% fractions are collected and further incubated with human IgG to remove FcR-bearing cells. The remaining cells are re-fractionated to provide an intermediate density cell (IDC) fraction that is relatively depleted of lower density monocytes and higher density lymphocytes.

The IDC fraction (approximately $1-5\times10^6$ cells per buffy coat representing an approximately 200-fold enrichment) typically consists of a mixture of T cell blasts, B cells, dendritic cells and natural killer cells in addition to presumed lineage precursors.

The human B4B gene was originally identified and cloned using a differential display PCR method comparing RNA isolated from IDC to RNA isolated from low and high density fractions of PBMC, as detailed in Example 2. A 101-basepair (bp) insert was expressed at detectable levels in the IDC fraction. The insert was also detected in bulk PBMC, under higher stringency conditions, using sequence-specific primers. The insert was not detected in the high or in the low density fraction, nor was it detected in EBV-transformed mature B cells.

The 101 bp PCR product was radiolabeled and used as a probe to obtain a full length 2.7 kb cDNA insert from a lambda phage cDNA library prepared from the IDC mRNA. This insert was subcloned into plasmid Bluescript IIKS which is carried by an *E. coli* (Top-10 strain) clone ("1-12# 6-29.BS";). clone are deposited in the Stanford University Blood Bank (Dr. Edgar Engleman, Palo Alto, Calif.). The full-length B4B cDNA (FIG. 1) contains a single open reading frame of 471 basepairs (bp) preceded by a 122-bp 5'-untranslated region (containing no alternative ATG translation initiation codons) and followed by a 3'-untranslated region of approximately 2.1 kb. The open reading frame (ORF) encodes a polypeptide of 157 amino acids with a calculated Mr of 17,542 daltons, four putative transmembrane-spanning (TM) domains and two potential asparagine-linked glycosylation sites, as indicated in the Figure. This sequence now appears in the EMBL, Genbank and DDBJ Nucleotide Sequence Databases under the accession number Z50751.

Using similar methods, a murine cDNA clone encoding the murine homologue of B4B has also been isolated (SEQ ID NO: 6; FIG. 3). This ORF cDNA encodes a polypeptide (SEQ ID NO: 7; FIG. 4) that exhibits 76% sequence identity with the human homologue at the amino acid level.

The human 2.7 kb cDNA was sequenced and used as a probe to identify a B4B genomic clone from a normal human genomic library. The gene was localized to human chromosome 20.

Information derived from the present disclosure is used to isolate cDNA's of other members of the B4B growth arrest gene family that form a part of the invention. It is also appreciated that, knowing now the sequence of the human and murine B4B genes, it is possible to (i) identify homologous DNA segments from human and other species, (ii) isolate homologous DNA segments from other tissues, and (iii) produce synthetic B4B genes, according to methods well known in the art. Specifically, such methods include, but are not limited to screening cDNA libraries using hybridization probes derived from the B4B gene sequences disclosed herein (e.g., SEQ ID NO: 1, SEQ ID NO: 2, SEQ ID NO: 6) or PCR-based screening techniques known in the art. (White). Conventional hybridization probes can be derived from any fragment of the B4B nucleotide sequences presented herein, or can include the entire sequences of such B4B polynucleotides, but are generally at least 20 nucleotides in length. They are preferably derived from the open reading frame and are between about 100 and 500 nucleotides in length. Design and construction of such probes are within the knowledge of persons skilled in the art. Similar techniques are used to characterize the sequence of other members of the B4B Growth Arrest Gene family, as described above.

The sequence of the 2.7 kb cDNA isolated from the lambda phage cDNA library was determined using an ABI Model 373 DNA Sequencer (Perkin Elmer/Applied Biosystems, Foster City, Calif.). The sequence of the 2.7 kb insert is shown as SEQ ID NO: 1 in FIG. 1. The deduced amino acid sequence of the open reading frame (ORF; nts 123–593; SEQ ID NO: 2) is shown as SEQ ID NO: 3 in FIG. 1.

2. Tissue localization of B4B a. Chromosomal Localization.

The chromosomal position of the human B4B gene was determined by fluorescence in situ hybridization in which a B4B genomic probe hybridized specifically to human chromosome 20, according to the methods detailed in Example 3. In a second experiment, a probe specific for the chromosome 20 centromere was cohybridized with the B4B probe and measurements of 10 cohybridized chromosomes 20 showed that the B4B gene resides at a position 48% of the distance from the centromere to the telomere of arm q, an area corresponding to the boundary between bands 20q12 and 20q13.1 (FIG. 2). Other genes known to reside in this region include those encoding the src oncogene, adenosine deaminase, bone morphogenetic protein-2a and the unsequenced loci for mature onset diabetes of the young and Fanconi's anemia. By comparison, the gene encoding PMP-22/gas-3 resides on Chromosome 17 at band q11.1 (Patel, Matsunami, Timmerman, Valentijin).

b. Tissue Distribution of B4B.

Expression of B4B mRNA appears to be restricted to the IDC fraction within peripheral blood; however, in studies carried out in support of the present invention, analysis of a multiple tissue Northern blot with the B4B probe detected a 2.7 kb mRNA species in virtually every tissue tested with the exception of brain, spleen and PBMC. The lack of a detectable signal from bulk PBMC, presumably due to reduced sensitivity as compared to PCR, is consistent with the apparent rare, IDC-restricted, expression of B4B within peripheral blood.

Antisera were raised against two synthetic peptides selected from the predicted amino acid sequence of B4B, based on the criterion of minimizing sequence conservation with PMP-22, a protein identified as having only 35% homology with human B4B and therefore not considered a part of the Growth Arrest Gene Product family. The peptide sequences are shown as italicized residues in FIG. 1. These two regions of B4B are predicted to reside in putative extracellular domains of the protein by analogy with other proteins containing four transmembrane (TM) domains (Wright). The affinity purified anti-Peptide 2 Ig recognized intact B4B protein of the expected size (18 kilodaltons) in radioimmunoprecipitation experiments whereas the anti-Peptide 1 Ig did not. Consequently, the anti-Peptide 1 Ig was subsequently used as a negative control. The anti-peptide antibodies were then used to examine a panel of normal human tissue sections by immunohistology. In contrast to the broad range of tissue distribution of B4B observed at the mRNA level, the only cells found to be positive by immunohistology were infrequent large cells lining the medullary sinuses in lymph node as compared to lymph node stained with anti-Peptide 1. Heart and placenta, as well as all other tissues tested (brain, lung, kidney, liver, bladder, colon, small intestine, stomach, adrenal medulla, thyroid, skin, spleen, thymus, tongue, prostate, testis, breast, uterus and ovary, were negative, using this detection method at the level of sensitivity described.

The interaction of anti-Peptide 2 antisera with lymph node cells was completely blocked by pre-incubation with excess free Peptide 2, indicating that the staining of lymph node cells with anti-Peptide 2 antisera is specific for B4B.

c. Distribution of B4B within the PBMC Fraction Cell surface phenotype of B4B+ cells.

Anti-Peptide 2 Ig reacted only with cells fixed with a combination of 5% paraformaldehyde and organic solvents, precluding flow cytometric analysis using this antibody. However, two-color immunofluorescence microscopy was performed with a limited panel of phenotypic markers which react with paraformaldehyde-fixed cells. The anti-B4B Ig was used to stain PBMC in which extremely rare (~0.01%) positive cells were observed, consistent with the existence of an equilibrium for B4B+ cells between lymph node and peripheral blood. To increase the frequency of B4B+ cells for ease of analysis, the interface cells of a 50% Percoll gradient were used for subsequent staining where B4B+ cell frequency was increased to 0.1–1.0%.

In studies carried out in support of the present invention, PBMC from normal donors were purified by LYMPHOPREP, fractionated over 50% PERCOLL (Pharmacia, Piscataway, N.J.) to enrich for B4B+ cells then incubated with a mixture of specific antibodies to determine the presence of cellular antigens. In further studies, cells were stained with anti-Peptide 2 Ig and mouse Ig specific for CD45 or with HLA-DR, $\mu$-chain, CD34, or CD68. Bound Ab was detected with a mixture of species-specific, cross-adsorbed PE-donkey-anti-rabbit IgG and biotinylated donkey-anti-mouse IgG followed by FITC-streptavidin. Representative fields of micrographs prepared from were photographed through PE or FITC filters to visualize B4B and the lineage markers, respectively, and were analyzed for assessment of double positivity versus mutual exclusion of expression of various lineage markers and B4B.

Staining of cells with pre-immune Ig and anti-Peptide 1 Ig did not result in a detectable signal. Staining with a combination of anti-Peptide 2 Ig and lineage subset mAb revealed that B4B+ cells coexpress CD45 and HLA-DR but are negative for cytoplasmic or surface $\mu$-chain, CD34, and CD68.

Fractionation of PBMC by immunoselection into immune cell phenotypic subsets followed by fixation and staining with anti-Peptide 2 Ig revealed that the B4B+ cells are CD19+, based on an approximate 10-fold enrichment of B4B+ cells, using the pan-B cell marker CD19. However, two-color analysis with anti-B4B and anti-CD20 revealed that B4B+ cells are negative for CD20 and represent a rare CD19+CD20− subset of B cells in peripheral blood. Positive immunoselection with mAb recognizing CD3 or CD16 and CD56 resulted in a reduction of B4B+ cell frequency to undetectable levels, thus confirming that B4B+ cells are CD3−CD16−CD56−.

The B4B cell surface marker expression pattern described above is consistent with an early B lineage phenotype based on expression of CD19, CD45 and HLA-DR but lack of CD3 (T cell), CD20 and cytoplasmic μ-chain (mature B cell), CD16 and CD56 (natural killer cell), CD68 (monocyte/macrophage) and CD34 (hematopoietic stem cell progenitor). Based on the hypothesis that B4B is expressed by progenitor/pre-B lineage cells, immunofluorescent microscopic analysis was performed on mononuclear cells of normal adult bone marrow, the compartment of origin for B lineage cells. The frequency of B4B+ cells was found to be greater than 100-fold higher (3–10%) as compared to their frequency in PBMC (0.01%).

d. Bone Marrow

Three-color flow cytometric analysis revealed presence of the previously undescribed CD19+CD20−CD34− phenotypic subset of pre-B lymphocytes in normal bone marrow. In two-parameter analysis of CD19 and CD20, normal bone marrow mononuclear cells contained 4.6% CD19+CD20− cells. When the CD19+CD20− cells were gated and analyzed for CD34 expression, two subsets were apparent with one co-expressing CD34 (0.9 % of total mononuclear cells) and the other negative for CD34 (3.7% of total mononuclear cells). This latter CD19+CD20−CD34− subset is consistent both in phenotype and in prevalence with the B4B+ subset as determined via immunofluorescent microscopy, described above.

B. Heterologous Expression of B4B

B4B antigens can be transfected into and heterologously expressed in eukaryotic cells, according to methods known in the art. In studies carried out in support of this aspect of the invention, COS-7 cells were transfected with B4B cDNA, isolated as described above, under dual control of a CMV early and a bacteriophage promoter t7 promoter or with CD4 cDNA as a control, according to standard methods well known in the art. When the cells were infected with recombinant vaccinia virus expressing the bacteriophage T7 RNA polymerase, which in turn could drive RNA transcription of the B4B cDNA directly in the cytoplasm, B4B protein was detected in approximately 60–80% of the cells comparable to that observed for CD4. The anti-B4B Ig was specific for B4B, since no signal was observed when it was used to stain vaccinia-infected CD4-transfected cells.

C. Gene Family

Figure 7A:
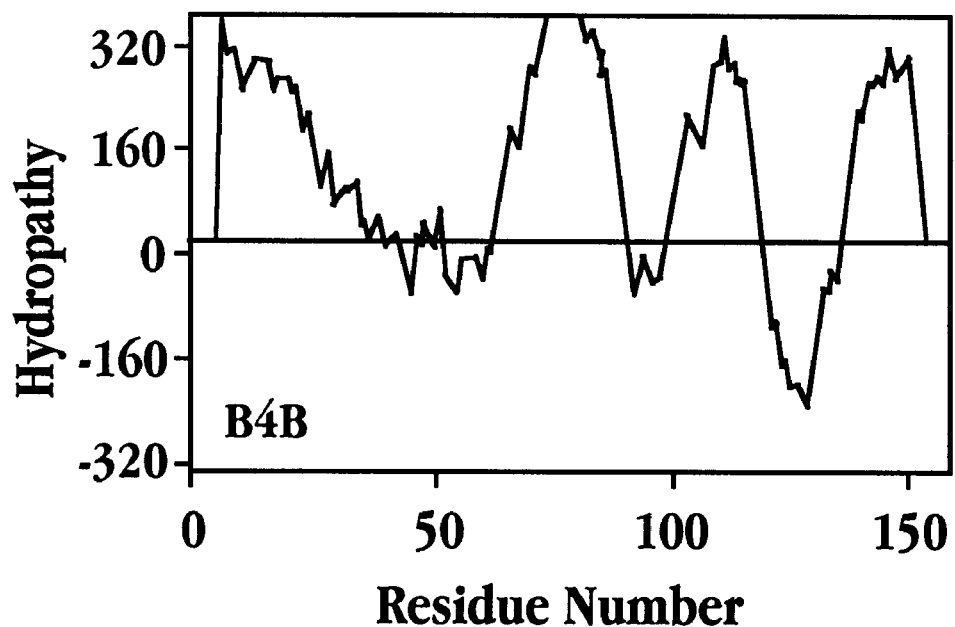
FIGS. 7(A and B) show a comparison of hydropathy analysis of B4B (A) and PMP-22 (B) proteins, where relative hydrophobicity (as determined using the hydropathy algorithm of the Geneworks version 2.45 software program) is directly proportional to the numerical scale of the ordinate.
Figure 7B:
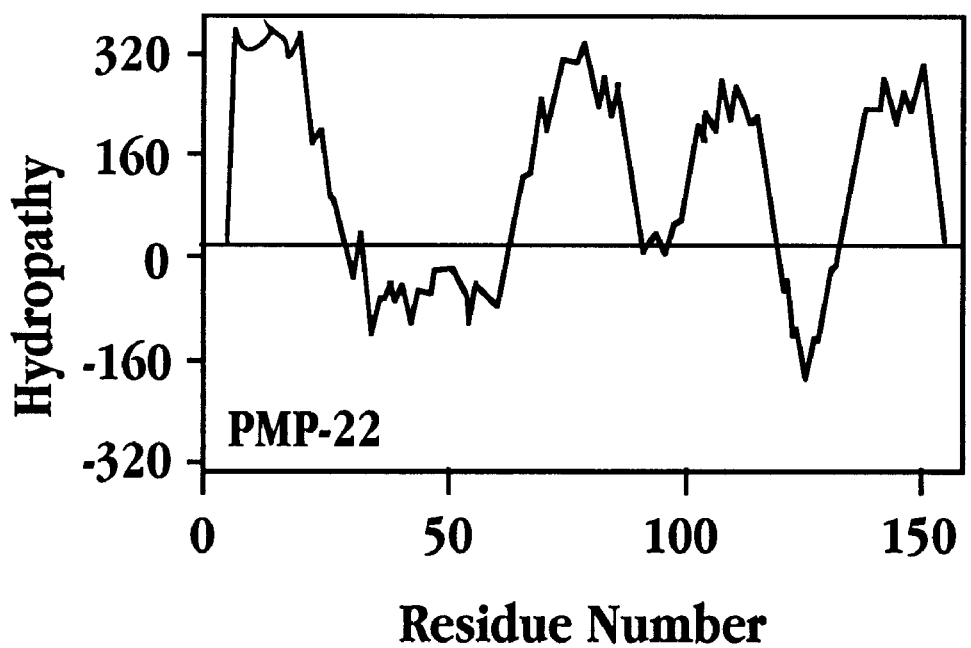

When compared for sequence homology (Geneworks software version 2.45, Intelligenetics Corp., Mountain View, Calif.) to the SwissProt protein sequence database (Rel. 31), the B4B protein sequence exhibits homology (35% identity at the amino acid level) with a single gene product, PMP-22/gas-3. No additional homologies were revealed when the B4B sequence was compared to the Genbank database (Rel. 88) at the DNA level. Hydropathy analysis of B4B and PMP-22 (FIGS. 7A and 7B) using the hydropathy algorithm of the Geneworks software package illustrates the dramatic conservation of overall domain structure.

This present invention therefore represents the first identification of a new growth arrest gene family. Members of this family include proteins exhibiting at least 50%, and preferably at least 75% amino acid sequence homology with either of the B4B gene products described herein (SEQ ID NO: 3; SEQ ID NO: 6), covering proteins which have: (i) four distinct regions of consisting predominantly of hydrophobic amino acids, (ii) more than 50%, and preferably more than 75% sequence homology with the B4B gene product shown as SEQ ID NOS: 3 and 6, herein, and (iii) ability to arrest growth of cells in which the protein is expressed.

III. Utility

A. Cell Growth Inhibitor

Figure 6B:
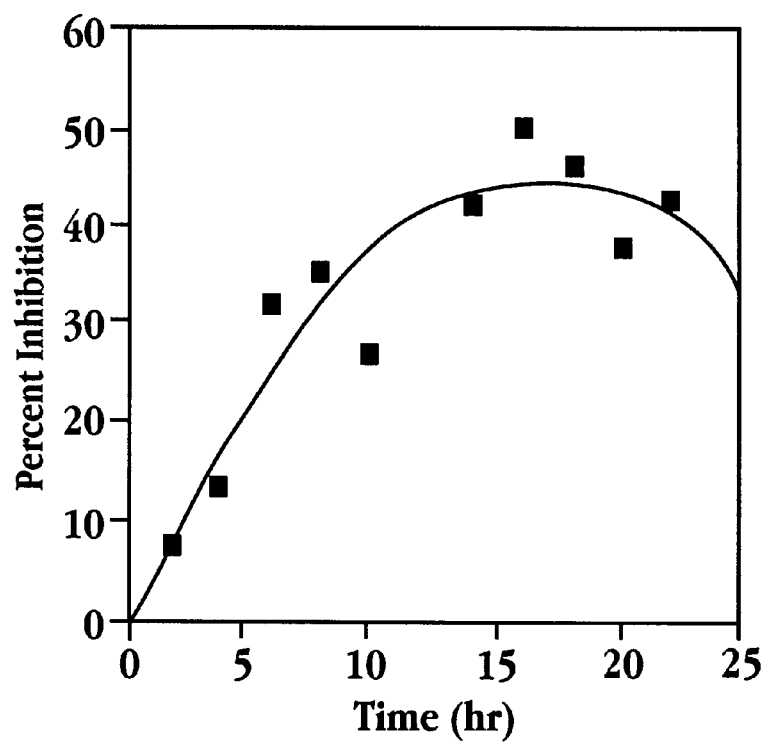
FIG. 6B shows kinetics of B4B-induced growth arrest of cells.

In experiments carried out in support of the invention, it was found that expression of B4B protein inhibited cellular proliferation. COS-7 cells were transfected with B4B or CD4 as a control and infected with vaccinia/T7 as described above. The transfected cells were cultured for 15 hr then were pulsed with [$^3$H]thymidine (TdR) and harvested to quantitate the proliferative response. Cells were cultured for 18 hr with [$^3$H]TdR present during the final three hours prior to harvesting. The data in FIG. 6A show thymidine incorporation as the mean of quadruplicate determinations. FIG. 6B shows the kinetics of B4B-induced growth arrest. Cells were transfected and infected with vaccinia virus as described in Example 8, and cultured for the time periods indicated on the (x-axis) with the final two hours constituting the [$^3$H]TdR pulse.

As shown in FIG. 6A, expression of B4B protein in COS-7 cells inhibited cellular proliferation by greater than 50% as compared to cells expressing CD4 ($p < 0.001$). The kinetics of inhibition (FIG. 6B) exhibited a biphasic pattern consistent with the expected effect of combining the increasing specific inhibition due to B4B expression during the early phase of the experiment followed by the non-specific inhibition induced by late-stage vaccinia virus infection.

The observation that B4B expression inhibits cellular proliferation can be exploited in a number of ways. First, the gene can be inserted into cells to control or inhibit proliferation, as discussed below.

For example, such expression can be effected by retroviral transduction of the B4B gene into the cells of interest. Alternatively, any of the other methods for gene transfer known in the art, such as lipofection, calcium-phosphate precipitation, DEAE-mediated transfection, electroporation, Adenoviral or Adeno-associated virus-mediated gene transfer, can be used to transfer B4B into target cells.

Such methods of introduction may be incorporated into gene therapeutic methods, as discussed below. For example, U.S. Pat. No. 5,399,346, incorporated herein by reference, describes insertion into lymphocytes of genes of interest for purposes of targeting cells to specific tissue sites. Likewise, U.S. Pat. No. 5,470,730, incorporated herein by reference, teaches methods for genetic manipulation of cytotoxic T-lymphocytes.

B. Cell Markers

An important feature of the present invention is the recognition that the B4B gene product is expressed as an antigen on a small, or "rare", subset of B cells. The presence of such cells in the general circulation or in the lymph serves as a diagnostic marker for a cancerous or pre-cancerous condition. In addition, the presence of such cells in circulation serves as an indicator of a particular immune state. Accordingly, antibodies and gene diagnostic reagents formed in accordance with the teachings provided herein, and according to methods well known in the diagnostic arts, can be used in the detection of such cells for diagnostic purposes. Such methods are illustrated in Examples 4–7 herein.

For example, a diagnostic test can be constructed using a standard ELISA format using the anti-B4B peptide antibodies prepared as described in Example 5 herein. The antibodies are coated onto microtiter plates to form a cell capture assay, according to methods known in the art. Fluids containing B4B-positive cells are then incubated in the microtiter wells for a period of time sufficient to effect capture of the cells. Detection of cells bound can be achieved by subsequently adding a labeled antibody directed to B4B or another antigen present on the cells, such as CD19. Alternatively, detection of the antigen may be accomplished by PCR methods or other equivalent methods known in the art, taking advantage of the constructs and sequences disclosed herein.

C. Gene Therapy

B4B protein is expressed in B-lymphocytes which undergo non-productive VDJ rearrangement of their immunoglobulin gene locus. In these cells B4B may serve as a growth arrest gene for an otherwise dysfunctional cell type. Conversely, a defective or defunct B4B gene that fails to express B4B protein in pro-B cells which undergo non-productive VDJ rearrangement may lead to the outgrowth of malignant clones. A substantial portion of Pro-B-Cell leukemias show the phenotype that is typically associated with B4B expression and are thus candidates for a malignancy that might be caused by a defunct B4B gene. In this disease setting, a gene therapy approach using insertion of a healthy B4B allele into cells carrying faulty B4B alleles prevents development of pro-B-cell leukemia and other malignancies.

Insertion of B4B into cells to be used therapeutically has additional advantages that are recognized by the present invention. For example, B4B can be inserted in a vector that also includes a regulatable promoter to form a "suicide inhibitor" cassette. Here, expression of B4B could be induced by exposing the cells to an exogenous chemical activator of the promoter, such as ganciclovir, in order to arrest expansion of the cells. Such a composition may be useful when it is desirable to expand cells in vitro or in vivo, then arrest proliferation. Skin cells grown in culture for grafting might benefit from such a construct, as might lymphocytes which carry, for example, a heterologous cytokine gene for expression in vivo.

Such gene therapy can be carried out according to methods now known in the art, and as particularly described in U.S. Pat. Nos. 5,399,346, 5,470,730 and 5,252,479, and by Yang (1996), all of which are incorporated herein by reference.

The following examples illustrate, but in no way are intended to limit the present invention.

EXAMPLE 1

Isolation of Intermediate Density Cell (IDC) Fraction

PBMC were isolated from buffy coat fractions of normal adult blood donors using Lymphoprep (Gibco BRL, Gaithersburg, Md.) according to the supplied instructions. PBMC were then fractionated into low and high density fractions on a four-step discontinuous Percoll (Pharmacia LKB, Uppsala, Sweden) gradient (15) consisting of steps of 30%, 40%, 50.5% and 75% Percoll. The low density cell fraction was that recovered from the 50.5% step interface. The 75% step pellet was recovered, cultured overnight in RPMI 1640/10% pooled human serum and fractionated over a 15.5% metrizamide gradient (Gibco BRL) and the pellet fraction was used as the high density cell fraction. The 50.5% Percoll interface fraction was cultured overnight on petri dishes coated with human IgG to remove FcR-bearing cells and refractionated on a 14% metrizamide gradient. The resulting interface was used as the intermediate density cell, (IDC) fraction.

EXAMPLE 2

Cloning of B4B

The B4B gene was identified and cloned by differential display PCR and cDNA. Poly(A)+ RNA was purified from the IDC, low density and high density cell fractions isolated according to the method described in Example 1, and from the EBV-transformed lymphoblastoid cell line REM (Liu et al., 1990) using the Fast Track Kit (Invitrogen, San Diego, Calif.). Poly(A)+ RNA was reverse transcribed into cDNA using oligo(dT) and the cDNA Copy Kit (Invitrogen) and ligated to non-self-complementary Bst XI adaptors for insertion into a derivative of the pcDNA I plasmid (Invitrogen) digested with Bst XI. The ligated inserts were used to transform E. coli strain MC1061 by electroporation and resulted in cDNA libraries ranging from 0.5 to $2.0 \times 10^6$ independent clones. Differential display PCR was performed according Liang and Pardee except that purified plasmid DNA from amplified cDNA libraries was used instead of poly(A)+ RNA as template. PCR conditions were as follows using a DNA Thermal Cycler (Perkin Elmer, Norwalk, Conn.): 94° C. for 30 seconds, 42° C. for 60 seconds and 72° C. for 30 seconds for a total of 40 cycles followed by elongation at 72° C. for 5 minutes. Bands uniquely displayed by the IDC library were isolated from the PAGE gel, reamplified by PCR using the same conditions and cloned into PCRII (Invitrogen) and sequenced. DNA sequences were compared to the Genbank database and those found to be novel were further characterized by synthesizing 30-mer sequence specific primer pairs and screening the four cDNA libraries along with the insert plasmid DNA as a positive control using the following PCR conditions: 94° C. for 60 seconds, 60° C. for 60 seconds, 72° C. for 60 seconds for a total of 30 cycles followed by elongation for 5 min at 72° C.

In order to obtain a full-length cDNA clone, the 101-bp B4B insert was labeled with [32P]dGTP and [32P]dCTP using a random hexamers labeling kit (Boehringer Mannheim, Indianapolis, Ind.) and used to probe a lambda phage cDNA library prepared from the IDC mRNA using the Lambda Superscript and Packaging Kits (Gibco BRL) in E. coli according to the supplied instructions. Of a total of $1 \times 10^6$ plaques screened, four were selected for secondary screening and one clone containing a 2.7 kb insert was selected for further analysis. The insert was subcloned into pBluescript II KS(+) (Stratagene, San Diego, Calif.) and sequenced using an ABI 373 DNA Sequencer (Applied Biosystems, Foster City, Calif.). An E. coli clone was isolated that contains a 2.7 kB insert of cDNA that includes the B4B sequence in a Bluescript II KS Plasmid. This clone, labeled "1-12#6-29.BS" is deposited in the Stanford University Blood Bank (Dr. Edgar Engleman, Palo Alto, Calif.).

EXAMPLE 3

Identification of Genomic Clones by Fluorescence in situ Hybridization

The 2.7 kb B4B cDNA insert described in Example 2 was used as a probe to identify a B4B genomic clone from a normal human genomic DNA library using the P1 phage system (BIOS Laboratories, New Haven, Conn.). The B4B genomic clone was labeled with biotin dUTP by nick translation and hybridized to normal human metaphase chromosomes according to standard techniques. The hybridized probe was detected with avidin-FITC, and the chromosomes were counterstained with propidium iodide. In a second experiment, a human chromosome 20-specific probe was cohybridized with the B4B probe to determine the subchromosomal localization of the B4B gene. A total of 80 metaphase cells were analyzed and 73 exhibited specific signal.

EXAMPLE 4

Localization of Expression of B4B

A. Northern Analysis

The B4B cDNA insert was labeled as for phage library screening and used to probe nylon filters containing electrophoretically resolved poly(A)+ RNA from various normal human tissues (Clontech, Palo Alto, Calif.) according to the manufacturer's instructions. The filters were then stripped and reprobed with the supplied b-actin cDNA. Radioactive bands were visualized according to standard techniques (Ruegg et al., 1995).

B. Immunohistology

Microscope slides containing sections of formalin-fixed paraffin-embedded normal human tissues (BioGenex, San Ramon, Calif.) were deparaffinized according to the supplied instructions and nonspecific binding sites blocked by incubation in 5% nonfat dry milk/20% normal goat serum in Tris buffered saline for 20 minutes. Anti-peptide Ig ($2\mu g/ml$) diluted in blocking buffer was then added and allowed to incubate for 45 minutes followed by washing in Tris buffered saline. For blocking studies with excess free peptide, anti-Peptide 2 Ig was pre-incubated with free Peptide 2 (1 mg/ml) for 20 minutes and then the mixture was added to the tissue section. Bound Ig was detected using biotinylated goat-anti-mouse Ig followed by avidin-alkaline phosphatase (BioGenex). Positive cells were visualized with Fast Red substrate and counterstained with hematoxylin and mounted for photomicroscopy.

EXAMPLE 5

Production of B4B Peptide Antibodies

B4B-derived peptides, Peptide 1 (CSDSLSYASEDALK; SEQ ID NO:4) and Peptide 2 (SHYANRDGTQYHH; SEQ ID NO:5), were synthesized (BioSynthesis, Lewisville, Tex.) and conjugated to keyhole limpet hemocyanin (KLH) via the N-terminal cysteine residue using the Inject Activated Immunogen Conjugation Kit (Pierce Chemical, Rockford, Ill.). The KLH-conjugated peptides were used to immunize rabbits (EL Labs, Soquel, Calif.) and sera were collected after a total of three immunizations. Peptide-specific Ig was affinity purified from whole sera by passage over columns derivatized with either Peptide 1 or Peptide 2 using the ImmunoPure Ag/Ab Immobilization Kit (Pierce) according to the manufacturer's instructions. Affinity purified anti-Peptide Ig was used for all subsequent studies.

EXAMPLE 6

In vitro Production of B4B Protein

B4B protein was transcribed and translated in vitro using the TNT Kit (Promega, Madison, Wis.) in the presence of [35S]cysteine. Reaction mixtures were then solubilized in 1% Triton X-100/0.5% deoxycholate/0.1% SDS. Anti-peptide Ig was added to a final concentration of 2 $\mu$g/ml and immune complexes collected on Protein G-Sepharose (Zymed, South San Francisco, Calif.). Immunoadsorbed antigen was released by boiling in SDS-PAGE sample buffer containing 5% 2-mercaptoethanol, resolved on a 15% SDS-PAGE gel and radioactive bands were visualized as described (Ruegg et al., 1992).

EXAMPLE 7

Immunofluorescent Microscopy

PBMC were either further enriched for B4B+ cells by using the interface fraction from 50% Percoll gradients and analyzed directly or instead fractionated by antibody panning on petri dishes according to the method described by Engleman, et al., (1981) prior to attachment to microscope slides. Bone marrow aspirates from normal adult donors were processed by Lymphoprep prior to fixation on microscope slides. Based on an observation that only fixation by the combination of 5% paraformaldehyde and organic solvent revealed the B4B Peptide 2 epitope(s), all leukocyte preparations were fixed as follows: viable cells were allowed to attach to microscope slides coated with poly-L-lysine (Sigma Chemical Co., St. Louis, Mo.) for 15 minutes, incubated in 5% paraformaldehyde for five minutes followed by 50% acetone/50% methanol for five minutes, rehydrated in Tris buffered saline and nonspecific binding sites blocked as for tissue sections above. Unless otherwise noted, all mAb used in immunofluorescence microscopy were from Dako (Carpinteria, Calif.) with the exception of anti-CD34 (Amac, Inc., Westbrook, Me.). For immunofluorescence microscopy of COS-7 cell transfectants, cells were grown on glass coverslips then fixed and stained exactly as for leukocytes.

Anti-Peptide 1 or anti-Peptide 2 Ig was reacted with formalin-fixed, paraffin-embedded human tissues, visualized with biotinylated goat-anti-rabbit Ig and avidin-conjugated alkaline phosphatase followed by Fast Red substrate and counterstaining with hematoxylin. Lymph node was stained with anti-Peptide 1 as a negative control, anti-Peptide 2 or anti-Peptide 2 pre-incubated with excess free Peptide 2. Heart, placenta and other tissues were also stained with anti-Peptide 2.

In two-color analysis experiments, anti-Peptide 2 Ig (rabbit) was used in combination with mouse mAb, and each was specifically detected using a cocktail of species-specific, cross-adsorbed phycoerythrin (PE)4-conjugated donkey-anti-rabbit IgG and biotinylated donkey-anti-mouse IgG followed by FITC-conjugated streptavidin (Jackson ImmunoResearch, West Grove, Pa.). Cells were examined and photographed using a Zeiss Axiovert 100 fluorescence microscope (Carl Zeiss Inc., Thornwood, N.J.). For immunoselected cell lineage subsets, positive selection was performed using anti-CD3 (OKT3), anti-CD19 (Caltag, South San Francisco, Calif.) or a combination of anti-CD16 and anti-CD56 (Caltag). Panning on petri dishes coated with goat-anti-mouse IgG was performed as described by Engleman, et al. (1981).

EXAMPLE 8

Flow Cytometric Experiments

Normal bone marrow was fractionated on Lymphoprep and interface cells were blocked for FcR binding with D-PBS/20% normal goat serum followed by staining with fluorescent labeled anti-CD34-FITC (Becton-Dickinson, Inc., San Jose, Calif.), anti-CD19-Tricolor or anti-CD20-PE (Caltag, Inc., South San Francisco, Calif.) or irrelevant isotype matched controls. Analysis was performed using a FACScan flow cytometer (Becton-Dickinson) where quadrant gates were set to exclude 99.9% of cells stained with isotype controls (irrelevant isotype-matched control mAb). Results are shown in FIG. 5, where panel A shows cells analyzed for expression of CD19 (x-axis) and CD20 (y-axis). Panel B shows cells in the lower right quadrant (CD19+CD20−) of panel A replotted for expression of CD19 (x-axis) and CD34 (y-axis). Percentage values (4.6%, 3.7%) refer to the fraction of total cells bearing the corresponding phenotype. Nonviable cells were excluded by forward and side scatter.

EXAMPLE 9

Transient Expression in COS-7 Cells

COS-7 cells were transfected via electroporation with B4B or CD4 (irrelevant control) cDNA under dual control of the CMV immediate early and bacteriophage T7 promoters available in the pcDNA plasmid (Invitrogen). Cells were either infected immediately with recombinant vaccinia virus expressing the T7 RNA polymerase, vTF7-3 (21), or not infected.

EXAMPLE 10

Cell Proliferation Assay

For proliferation assays, cells ($2\times10^4$ per well) were plated in 96-well flat bottom plates and incubated at 37° C. for the amount of time specified. Cultures were pulsed with [3H]TdR (1 $\mu$Ci per well) and incorporated thymidine was measured using a 1205 BetaPlate (Wallac, Turku, Finland) where background readings averaged 12 cpm.

Percent inhibition was calculated using the following formula:

$$\% \text{ Inhibition}=(1-(\text{B4B cpm}/\text{CD4cpm}))\times100$$

A second order polynomial curve was fitted to the data to model a biphasic process of inhibition. Statistical significance was determined using Student's t-test.

While the invention has been described with reference to specific methods and embodiments, it will be appreciated that various modifications and changes may be made without departing from the invention.

What is claimed is:

1. An isolated DNA molecule comprising a nucleotide sequence that encodes a growth arrest gene product, wherein said DNA molecule includes the sequence presented as SEQ ID NO: 2.

2. An isolated DNA molecule comprising a nucleotide sequence that encodes a growth arrest gene product, wherein said DNA molecule includes the sequence presented as SEQ ID NO: 6.

3. An expression vector comprising a heterologous nucleotide coding sequence that encodes a B4B growth arrest gene product, wherein the coding region comprises the DNA sequence presented as SEQ ID NO: 2.

4. An expression vector comprising a heterologous nucleotide coding sequence that encodes a B4B growth arrest gene product, wherein the coding region comprises the sequence presented as SEQ ID NO: 6.

5. A eukaryotic cell comprising a heterologous nucleotide coding sequence that encodes a B4B growth arrest gene product, wherein said DNA molecule comprises a sequence selected from the sequences presented as SEQ ID NO: 2 and SEQ ID NO: 6.

6. A prokaryotic cell comprising a heterologous nucleotide coding sequence that encodes a B4B growth arrest gene product, wherein said heterologous coding region encodes the B4B gene product having the amino acid sequence selected from the sequences presented as SEQ ID NO: 3 and SEQ ID NO: 7.

7. A method of producing a cell that produces a B4B growth arrest gene product that inhibits proliferation of a host cell, comprising inserting into said cell an expression vector comprising a heterologous nucleotide coding sequence that encodes a B4B growth arrest gene product, wherein said nucleotide coding sequence comprises the sequence presented as SEQ ID NO: 2.

8. A method of producing a cell that produces a B4B growth arrest gene product that inhibits proliferation of a host cell, comprising inserting into said cell an expression vector comprising a heterologous nucleotide coding sequence that encodes a B4B growth arrest gene product, wherein said nucleotide coding sequence comprises the sequence presented as SEQ ID NO; 6.

* * * * *